US011369413B2

(12) United States Patent
Murphy

(10) Patent No.: US 11,369,413 B2
(45) Date of Patent: Jun. 28, 2022

(54) INTRODUCER SHEATH HAVING A MULTI-LAYER HUB

(71) Applicant: ABIOMED, Inc., Danvers, MA (US)

(72) Inventor: John Murphy, North Reading, MA (US)

(73) Assignee: ABIOMED, INC., Danvers, MA (US)

( * ) Notice: Subject to any disclaimer, the term of this patent is extended or adjusted under 35 U.S.C. 154(b) by 0 days.

(21) Appl. No.: 16/895,455

(22) Filed: Jun. 8, 2020

(65) Prior Publication Data

US 2020/0367930 A1 Nov. 26, 2020

Related U.S. Application Data

(63) Continuation of application No. 15/438,917, filed on Feb. 22, 2017, now Pat. No. 10,709,476.
(Continued)

(51) Int. Cl.
*A61B 17/34* (2006.01)
*A61M 25/06* (2006.01)
(Continued)

(52) U.S. Cl.
CPC ...... *A61B 17/3468* (2013.01); *A61B 17/3423* (2013.01); *A61M 25/0668* (2013.01);
(Continued)

(58) Field of Classification Search
CPC ............ A61B 17/3401; A61B 17/3423; A61B 17/3468; A61B 2017/0046; A61M 60/148; A61M 25/0668
See application file for complete search history.

(56) References Cited

U.S. PATENT DOCUMENTS 4,699,611 A   10/1987  Bowden
5,139,486 A    8/1992  Moss
(Continued)

FOREIGN PATENT DOCUMENTS

EP   1444000 A2   8/2004
EP   2335764 A1   6/2011
(Continued)

OTHER PUBLICATIONS

International Search Report PCT/EP2016/050234 dated May 20, 2016 (5 pages).
(Continued)

*Primary Examiner* — Nicholas J Plionis
(74) *Attorney, Agent, or Firm* — Botos Churchill IP Law LLP

(57) ABSTRACT

An introducer assembly includes an elongate sheath sized for insertion into a blood vessel of a patient and a hub. The hub can be coupled to a proximal portion of the sheath and can include a first hub portion and a second hub portion. The hub can include various features to facilitate breaking apart or separating the introducer assembly from a patient. For example, the first hub portion can have a first notch which can facilitate breaking, splitting, or fracturing the hub. The second hub portion can partially surround the first hub portion and can include two wings and an opening disposed above the first notch. The first hub portion can be formed from a first material and second hub portion can be formed from a second material. In some embodiments, the second material can be stiffer than the first material to facilitate fracturing the hub.

19 Claims, 7 Drawing Sheets

Related U.S. Application Data

(60) Provisional application No. 62/298,171, filed on Feb. 22, 2016.

(51) Int. Cl.
*A61M 60/135* (2021.01)
*A61M 60/148* (2021.01)
*A61B 17/00* (2006.01)

(52) U.S. Cl.
CPC ........ *A61M 60/135* (2021.01); *A61M 60/148* (2021.01); *A61B 17/3401* (2013.01); *A61B 2017/0046* (2013.01)

(56) References Cited

U.S. PATENT DOCUMENTS

| | | | |
|---|---|---|---|
| 5,167,634 A | 12/1992 | Corrigan et al. | |
| 5,234,425 A | 8/1993 | Fogarty et al. | |
| 5,304,142 A | 4/1994 | Liebl et al. | |
| 5,320,611 A | 6/1994 | Bonutti et al. | |
| 5,395,341 A | 3/1995 | Slater | |
| 5,397,310 A | 3/1995 | Chu et al. | |
| 5,407,430 A | 4/1995 | Peters | |
| 5,488,960 A | 2/1996 | Toner | |
| 5,489,273 A * | 2/1996 | Whitney | A61M 25/0637 604/160 |
| 5,492,530 A | 2/1996 | Fischell et al. | |
| 5,536,255 A | 7/1996 | Moss | |
| 5,573,517 A | 11/1996 | Bonutti et al. | |
| 5,653,697 A | 8/1997 | Quiachon et al. | |
| 5,911,702 A | 6/1999 | Romley et al. | |
| 5,935,122 A | 8/1999 | Fourkas et al. | |
| 5,971,993 A | 10/1999 | Hussein et al. | |
| 6,197,016 B1 | 3/2001 | Fourkas et al. | |
| 6,338,730 B1 | 1/2002 | Bonutti et al. | |
| 6,428,556 B1 | 8/2002 | Chin | |
| 6,613,038 B2 | 9/2003 | Bonutti et al. | |
| 6,692,462 B2 | 2/2004 | Mackenzie et al. | |
| 6,814,715 B2 | 11/2004 | Bonutti et al. | |
| 6,887,417 B1 * | 5/2005 | Gawreluk | A61M 25/0009 264/328.1 |
| 7,025,746 B2 | 4/2006 | Tal | |
| 7,422,571 B2 | 9/2008 | Schweikert et al. | |
| 7,524,305 B2 | 4/2009 | Moyer | |
| 7,722,567 B2 | 5/2010 | Tal | |
| 8,147,452 B2 | 4/2012 | Nardeo et al. | |
| 8,597,277 B2 | 12/2013 | Lenker et al. | |
| 8,672,888 B2 | 3/2014 | Tal | |
| 8,758,402 B2 | 6/2014 | Jenson et al. | |
| 9,884,169 B2 | 2/2018 | Bierman et al. | |
| 10,709,476 B2 * | 7/2020 | Murphy | A61M 25/0668 |
| 2003/0088264 A1 | 5/2003 | Spohn et al. | |
| 2004/0064147 A1 | 4/2004 | Struble | |
| 2004/0098020 A1 | 5/2004 | Nardeo | |
| 2005/0049628 A1 | 3/2005 | Schweikert et al. | |
| 2005/0149105 A1 | 7/2005 | Leeflang et al. | |
| 2006/0135981 A1 | 6/2006 | Lenker et al. | |
| 2006/0287574 A1 | 12/2006 | Chin | |
| 2008/0046005 A1 | 2/2008 | Lenker et al. | |
| 2008/0051734 A1 | 2/2008 | Bonutti et al. | |
| 2008/0051821 A1 | 2/2008 | Gephart | |
| 2008/0082165 A1 | 4/2008 | Wilson et al. | |
| 2009/0143739 A1 | 6/2009 | Nardeo et al. | |
| 2009/0177163 A1 | 7/2009 | King et al. | |
| 2009/0192463 A1 * | 7/2009 | Nardeo | A61M 25/0668 604/164.01 |
| 2009/0240202 A1 | 9/2009 | Drasler et al. | |
| 2010/0268196 A1 | 10/2010 | Hastings et al. | |
| 2013/0131718 A1 | 5/2013 | Jenson et al. | |
| 2013/0310765 A1 | 11/2013 | Stephens et al. | |
| 2013/0317438 A1 | 11/2013 | Ellingwood et al. | |
| 2013/0317481 A1 | 11/2013 | Ellingwood et al. | |
| 2014/0025003 A1 | 1/2014 | Kimmel et al. | |
| 2015/0151086 A1 * | 6/2015 | Teoh | A61M 25/0612 604/263 |
| 2016/0066948 A1 | 3/2016 | Ellingwood et al. | |
| 2016/0220358 A1 | 8/2016 | Wilson et al. | |
| 2016/0354583 A1 | 12/2016 | Ellingwood et al. | |
| 2017/0056063 A1 | 3/2017 | Ellingwood et al. | |
| 2017/0238965 A1 | 8/2017 | Murphy | |
| 2017/0281908 A1 | 10/2017 | Ellingwood et al. | |

FOREIGN PATENT DOCUMENTS

| | | |
|---|---|---|
| EP | 2623151 A1 | 8/2013 |
| EP | 3311873 A1 | 4/2018 |
| JP | H02102667 A | 4/1990 |
| JP | H03292963 A | 12/1991 |
| JP | 2001340469 A | 12/2001 |

OTHER PUBLICATIONS

Office Action from corresponding Japanese Application No. 2018-544150 dated Apr. 1, 2021 (8 pages).

Examination report No. 1 corresponding to Australian Application No. 20177223417 dated Feb. 9, 2021 (4 pages).

* cited by examiner

INTRODUCER SHEATH HAVING A MULTI-LAYER HUB

CROSS-REFERENCE TO RELATED APPLICATIONS

This application is a continuation of U.S. application Ser. No. 15/438,917, filed Feb. 22, 2017, allowed, which application claims priority to U.S. provisional application No. 62/298,171, filed Feb. 22, 2016, the contents of which are hereby incorporated herein by reference in their entirety.

BACKGROUND

Patients with cardiac ailments are sometimes treated with a percutaneous mechanical circulatory support device, also commonly referred to as a heart pump, configured to assist the natural cardiac pump function or to replace natural cardiac pump function by a continuous pumping operation. These heart pump assemblies can be introduced surgically or percutaneously during a cardiac procedure through the vascular system, such as through blood vessels. In one common approach, pump assemblies are inserted via a catheterization procedure through the femoral artery using an introducer sheath.

The introducer sheath can provide a reliable access point for the introduction of heart pump assemblies as well as a wide range of diagnostic and therapeutic interventional catheter-based devices. The introducer sheath can be inserted into an artery or vein, and the pump can be advanced through the introducer sheath into the patient. The introducer sheath can then be separated into two halves along a break wall and peeled away while the pump, catheter, and/or guidewire is left in place. This allows physicians to perform clinical procedures that require separation/removal of the introducer sheath without disturbing the position of a pump, catheter, guidewire, and/or other device that has been introduced into and should remain positioned inside of the body.

As percutaneous heart pumps have become larger and more sophisticated, the introducer sheaths for introduction of the pumps into the body have also necessarily become larger. The larger introducer sheath and hub assembly require a greater breaking force to split the hub of the introducer sheath (e.g., because the thickness of the break wall is greater). The increased break force can make fracturing the hub difficult and less reliable. Furthermore, the increased break force can lead to abrupt breaks of the hub which may undesirably jostle, dislodge, or damage the pump, and/or may in some cases cause discomfort or injury to the healthcare physician administering treatment.

SUMMARY

Disclosed herein is an introducer sheath having a multi-layer hub for percutaneous insertion of a heart pump. The hub can include two or more hub portions formed of different materials so as to reduce the break force required to split the peel-away introducer. The hub has a first hub portion and a second hub portion partially surrounding the first hub portion. The first hub portion includes one or more notches along which the hub is configured to split. The second hub portion includes wings or tabs positioned on either side of the hub which are used as leverage for applying the break force. The first hub portion may be formed of a soft material having a low ultimate strength, while the second hub portion may be formed of a relatively stiff material having an ultimate strength higher than that of the first hub portion. In such a configuration, the soft first hub portion allows the hub to be easily split along the notches in the first material, while the stiff second hub portion has stiff wings which provide improved leverage during breaking. The stiff wings do not bend or flex excessively when a force is applied, but instead transfer applied loads to the notches, thereby facilitating splitting of the introducer. The stiffer wings also reduce the amount of elastic energy that is stored when force is applied to the wings during splitting of the introducer hub. This reduces the sudden release of elastic energy when the hub is split, thereby reducing the risk of displacing or damaging the pump, or causing discomfort or injury to the patient or physician. Thus, by using two hub portions of differing material properties, the systems, methods, and devices described herein can facilitate splitting of the peel-away introducer sheath. By maintaining a low break force, the multilayer hub enables use of wider bore introducer sheathes which would otherwise be too difficult to split.

The second hub portion may be over-molded on the first hub portion. The overmolding may form a hemostatic bond between the first hub portion and the second hub portion. To strengthen the bond between the two portions, the first hub portion may also include ridges or grooves over which the second hub portion is molded. This can increase the amount of torque that the second hub portion can transmit to the first hub portion without failure of the bond. Additionally, the second hub portion may include an opening above the one or more notches in the first hub portion. This opening allows the first hub portion to easily split in the region of the notch or notches, thus preserving the low break force of the hub.

In one aspect, an introducer assembly comprises an elongate sheath and a hub. The elongate sheath is sized for insertion into a blood vessel of a patient and includes a longitudinal axis. The hub is coupled to a proximal portion of the sheath and comprises a first hub portion and a second hub portion. The first hub portion comprises a first notch. The second hub portion partially surrounds the first hub portion and comprises two wings and an opening disposed above the first notch. The first hub portion comprises a first material and the second hub portion comprises a second material, wherein the first material differs from the second material. In some implementations, the first material has a first ultimate strength and the second material has a second ultimate strength. In certain implementations, the second ultimate strength is greater than the first ultimate strength. In some implementations, the first material has a first stiffness and the second material has a second stiffness, the second stiffness being greater than the first stiffness.

In some implementations, the first notch is oriented parallel to the longitudinal axis of the elongate sheath. In certain implementations, the hub is configured to break at the first notch along the direction of the longitudinal axis of the elongate sheath. In some implementations, the elongate sheath has a longitudinal scoring parallel to the longitudinal axis of the elongate sheath. The elongate sheath may be configured to tear along the longitudinal scoring parallel to the longitudinal axis of the elongate sheath.

In some implementations, the first hub portion includes ridges. In some implementations, the first hub portion and the elongate sheath form a hemostatic bond. In certain implementations, the wings comprise a wide face and a narrow face and the wide face is normal to the longitudinal axis of the elongate sheath. In some implementations, the narrow face of the wings is normal to the longitudinal axis of the elongate sheath. In some implementations, the first hub portion further includes a second notch. In some implementations, the first hub portions include a first ridge and a second ridge which define edges of the first notch.

In some implementations, the first material has a hardness of about 45 Shore D. In certain implementations, the second material has a hardness of about 68-72 Shore D. In some implementations, the introducer hub has a minimum diameter of about 9 Fr. In other implementations, the introducer hub has a minimum diameter of about 26 Fr. In certain implementations, the first hub portion has a minimum thickness of about 0.1 mm at the first notch. In some implementations, the first hub portion has a maximum thickness of about 0.3 mm at the first notch.

In some implementations, the thickness of the first hub portion at the first notch is variable along a length of the notch. In some implementations, the thickness of the first hub portion at the first notch is greatest at a proximal end portion of the first notch. In some implementations, the thickness of the first hub portion at the first notch is between about 0.01 inches and 0.012 inches at the proximal end of the first hub. In some implementations, the thickness of the first hub portion at the first notch is between about 0.004 inches and 0.006 inches at a distal end portion of the first hub.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

Figure 1:
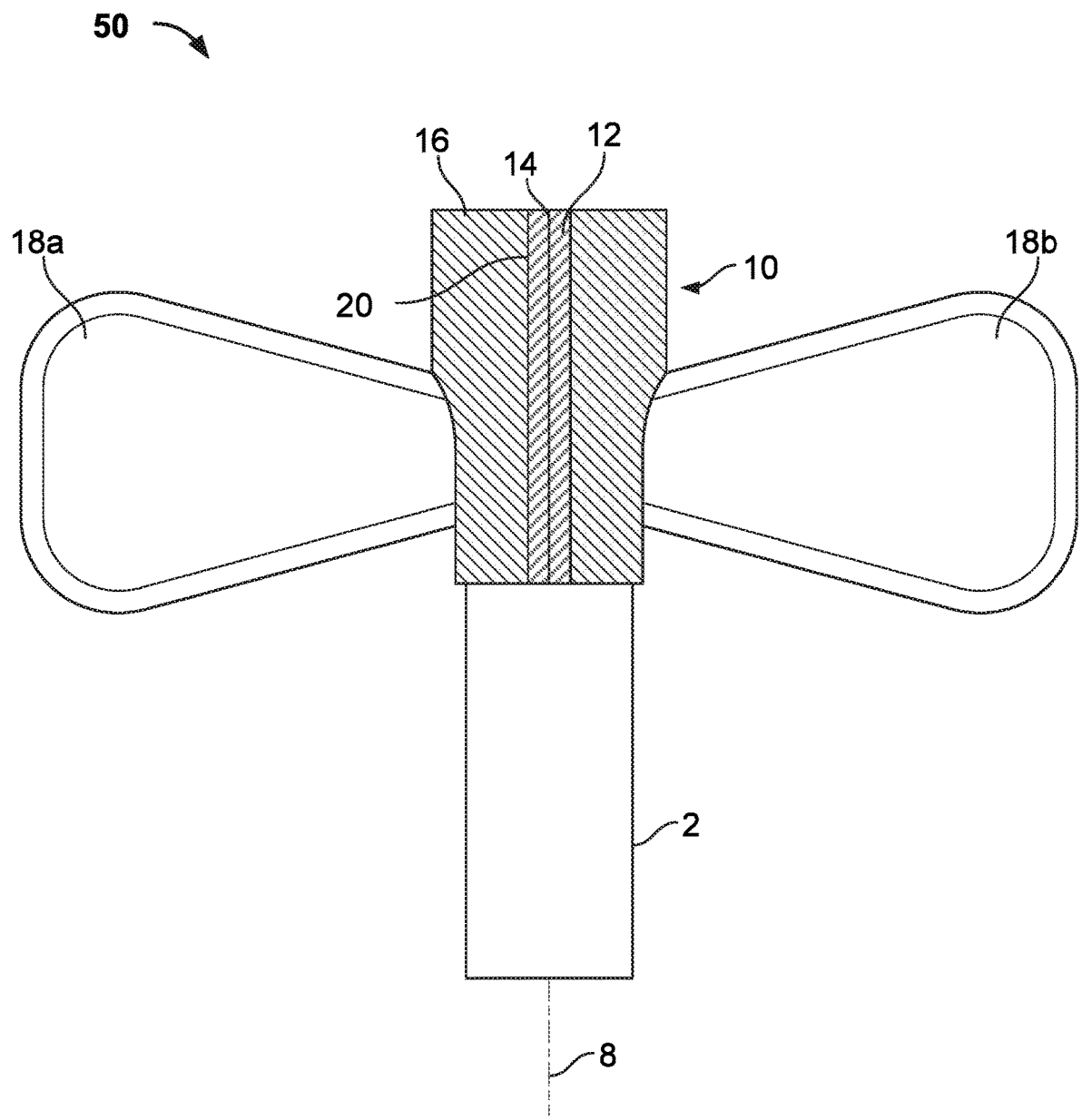
FIG. 1 shows a top view of an illustrative introducer hub assembly.

To provide an overall understanding of the systems, methods, and devices described herein, certain illustrative embodiments will be described. Although the embodiments and features described herein are specifically described for use in connection with introducer sheaths for percutaneous insertion of heart pumps, it will be understood that all the components and other features outlined below may be combined with one another in any suitable manner and may be adapted and applied to other types of introducer sheaths, other types of cardiac assist devices, or for the delivery of any suitable catheter, guide wire, surgical tool, or medical device.

The apparatus described herein includes an introducer and a hub assembly for the introducer (where the introducer can be used, e.g., for percutaneous insertion of a heart pump). The hub can have a first hub portion and a second hub portion partially surrounding the first hub portion. The first hub portion can include a notch along which the hub can be configured to fracture or split. The second hub portion can include wings or tabs positioned on opposite sides of the hub and may be used as leverage for applying the break force. The first hub portion can be formed of a soft material having a low ultimate strength, while the second hub portion can be formed of a relatively stiff material having an ultimate strength that is higher than an ultimate strength of the first hub portion. In such a configuration, the soft first hub portion can allow the hub to be easily fractured or split along the notch in the first material, while the wings of the stiff second hub portion provide improved leverage during breaking. The stiffness of the wings is selected so that the wings do not bend or flex excessively when pressure is applied and instead transfer applied loads to the notches, thereby facilitating splitting of the introducer. The stiffer wings can also reduce the amount of elastic energy that is stored when force is applied to the wings during splitting of the introducer hub. This reduces the sudden release of elastic energy when the hub is split, thereby reducing the risk of displacing or damaging the pump, and/or injuring the patient or physician. Thus, by using two hub portions with differing material properties, the systems, methods, and devices described herein can facilitate splitting of the introducer sheath. By maintaining a low break force, the multilayer hub enables use of introducer sheathes having larger dimensions and/or a larger bore which would otherwise be too difficult to split.

The hub assembly can be manufactured in various ways and can include different combinations of features. For example, the second hub portion can be over-molded on the first hub portion. The over-molding can form a bond between the first hub portion and the second hub portion that prevents blood from passing through the interface between the first hub portion and the second hub portion. In particular, the bond formed by the over-molding may be a chemical and/or molecular bond. If the first hub portion is formed of a polymer similar to a polymer from which the second hub portion is formed, the polymer chains of the two materials may cross-link at the interface between the first hub portion and second hub portion. Alternatively, the first and second hubs can be molded separately and then bonded together using any technique known in the art, such as using chemical adhesive. In either instance, the first hub portion may also include ridges or grooves to strengthen the bonding between the first and second hub portions by increasing the surface area for polymer cross-linking and/or to provide a mechanical interlock between the first and second hub portions. This can increase the amount of force that the second hub portion can transmit to the first hub portion without failure of the bond. For another example, the second hub portion may include an opening above the one or more notches in the first hub portion. This opening allows the first hub portion to easily split in the region of the notch, thus preserving the low break force of the hub. By maintaining a low break force, the systems, methods, and devices described herein thus allow introducer hubs to be made larger to accommodate large heart pumps while still breaking apart with application of a reasonable amount of force.

FIG. 1 shows a top-down view of the introducer hub assembly 50 including an elongate sheath 2 and a hub 10. The elongate sheath 2 is sized for insertion into a blood vessel of a patient and has a longitudinal axis 8. The hub 10 includes a first hub portion 12 having a first notch 14, and a second hub portion 16 having an opening 20 and two wings 18a and 18b. The opening 20 is disposed above the first notch 14. The first notch 14 in the first hub portion 12 is in some implementations aligned with or at least partially parallel to the longitudinal axis 8 of the elongate sheath 2. The second hub portion 16 partially covers the first hub portion 12. In some implementations, the second hub portion 16 is over-molded onto the first hub portion 12. The second hub portion 16 includes an opening 20 above the first notch 14 which exposes the first notch 14.

The first notch 14 formed in the first hub portion 12 provides a break wall at which a crack may be initiated in the hub 10 by applying force to the wings 18a and 18b. The first notch 14 may be formed in a first material having a relatively low ultimate strength break force. Furthermore, the first notch 14 may be formed such that a thickness of the first material at the bottom of the first notch 14 permits breaking of the hub 10 at the first notch 14 at a reasonably low force. Additionally, the shape of the notch 14 may concentrate stress to facilitate splitting of the hub 10 along the notch 14. In some implementations, the first hub portion 12 has a minimum thickness at the first notch 14 of 0.1 mm. In some implementations, the first hub portion 12 has a maximum thickness of 0.3 mm at the first notch 14. In some implementations the first hub portion 112 has a thickness at the first notch 14 of 0.075 mm, 0.08 mm, 0.09 mm, 0.1 mm, 0.15 mm, 0.2 mm, 0.25 mm, 0.3 mm, 0.35 mm, or any other suitable thickness.

The second hub layer 16 partially surrounding the first hub layer 12 allows the wings 18a and 18b to be formed from a stiffer material. The stiff wings 18a and 18b allow a healthcare professional to apply force, such as a manual force, to break the hub 10 at the first notch 14. After the hub is broken, the wings 18a and 18b can be pulled apart and used to peel away the introducer hub assembly 50 from the patient and any devices or guidewires extending through the vessel. In some implementations, the second hub portion 16 can be over-molded over the first hub assembly 12.

During use, the introducer hub assembly 50 facilitates insertion of a heart pump or other medical object into a blood vessel of a patient. The introducer hub assembly 50 is designed as a peel-away introducer. The elongate sheath 2 is inserted into a blood vessel of the patient and the heart pump is advanced through the hub 10 and through the elongate sheath 2 into the patient. During removal of the introducer hub assembly 50, the wings 18a and 18b can be grasped and a first force is applied by a user, e.g. a healthcare professional, toward the user to break the hub 10 along the first notch 14. A second force may then be applied in a direction opposite the first force to break the hub 10 along a second notch (not shown). The introducer hub assembly 50, including the hub 10 and elongate sheath 2, is then peeled away, leaving the heart pump or other medical object undisturbed within the blood vessel of a patient.

Figure 2:
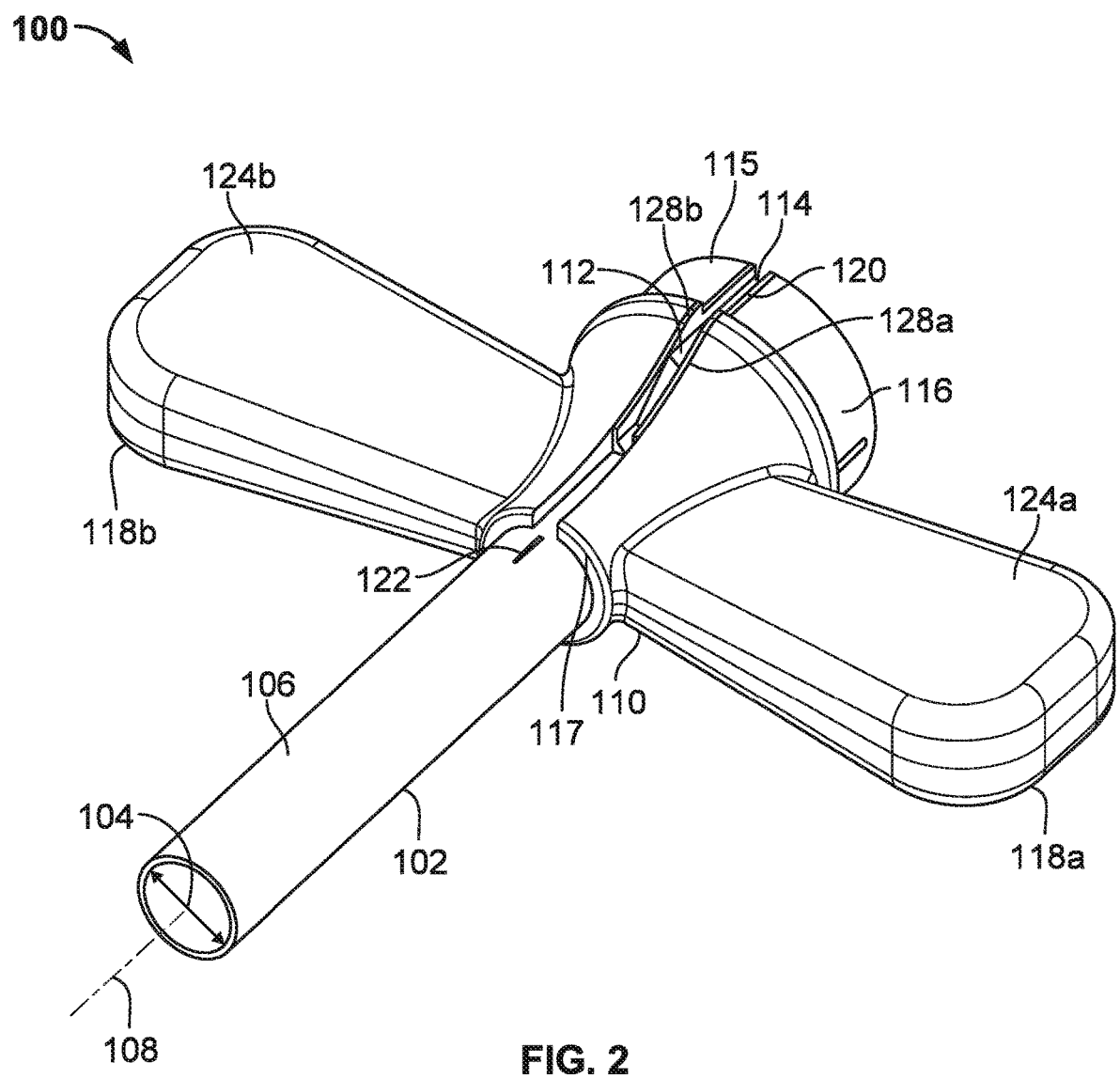
FIG. 2 shows a perspective view of an illustrative introducer hub assembly.

FIG. 2 shows a perspective view of an illustrative introducer hub assembly 100. The introducer hub assembly 100 includes an elongate sheath 102 and a hub 110. The hub 110 includes a first hub portion 112 and a second hub portion 116. The first hub portion 112 includes a first notch 114, a proximal end portion 115, and a distal end portion 117. The second hub portion 116 includes an opening 120 above the first notch 114 and two wings 118a and 118b. The elongate sheath 102 includes a longitudinal axis 108 and an internal diameter 104 which is sized to allow a heart pump or medical device to be inserted through the elongate sheath 102 and into a blood vessel of a patient. The internal diameter 104 of the elongate sheath may be 2 mm, 3 mm, 4 mm, 5 mm, 6 mm, 7 mm or any other suitable diameter. In some implementations, the inner diameter of the elongate introducer body 105 is compatible with devices that are 9 French (3 mm), 10 French (3.33 mm), 11 French (3.67 mm), 12 French (4 mm), 13 French (4.33 mm), 14 French (4.67 mm), 15 French (5 mm), 16 French (5.33 mm), 17 French (5.67 mm), 18 French (6 mm), 19 French (6.33 mm), 20 French (6.67 mm), 21 French (7 mm), 22 French (7.33 mm), 24 French (8 mm), 26 French (8.67 mm), or any other suitable diameter. The first hub portion 112 lies closest to an outer surface 106 of the elongate sheath 102. The first hub portion 112 includes a first notch 114 which is oriented to be parallel to the longitudinal axis 108 of the elongate sheath 102. The first hub portion 112 also includes a first ridge 128a and a second ridge 128b which extend up from surface of the elongate sheath 106, defining the first notch 114. The second hub portion 116 partially surrounds the first hub portion 112 except at an opening 120 over the first notch 114. In some implementations, the opening 120 is also over the first ridge 128a and second ridge 128b of the first hub portion 112 defining the first notch 114. The second hub portion 116 includes two wings 118a and 118b which extend outward on either side of the hub 110. Each of the two wings 118a and 118b is constructed to include a wide face 124a and 124b and a narrow face 125a and 125b. The two wings 118a and 118b may be oriented in a variety of directions. In some implementations, a wide face 124a and 124b of the wings 118a and 118b may be positioned to be normal to the longitudinal axis 108 of the elongate sheath 102. In other implementations, a narrow face 125a and 125b of the wings 118a and 118b may be positioned to be normal to the longitudinal axis 108 of the elongate sheath 102.

After the heart pump or medical device has been inserted into the patient, the introducer hub assembly 100 can be separated at the hub 110 along the length of the first notch 114 and at the elongate sheath 102 along the length of the longitudinal scoring 122. The wings 118a and 118b are designed to be gripped by a healthcare professional for removal. The healthcare professional applies force to the first and second wings 118a and 118b to part (e.g. "peel-away") the introducer assembly 100. This separates the hub 110 at the first notch 114 and the longitudinal scoring 120, fracturing/breaking the hub 110 and elongate sheath 102 in half. In some implementations, the wings 118a and 118b are designed to be pressed in a downward motion toward the elongate sheath 102 to break the hub 110 at the first notch 114. In such implementations, the wide face 124a and 124b of the wings 118a and 118b may be oriented to be normal to the longitudinal axis 108 of the elongate sheath 102. In other implementations, the narrow face 125a and 125b of the wings 118a and 118b may be positioned to be normal to the longitudinal axis 108 of the elongate sheath 102 and may be designed such that forcing the two wings 118a and 118b toward each other facilitates the breaking of the first notch 114. Once the hub 110 has been broken at the first notch 114, each of the wings 118a and 118b may be peeled away from each other to remove the hub 110. The elongate sheath 102 may also include a longitudinal scoring 122 parallel to the longitudinal axis 108 in line with the first notch 114 in the hub 110. The elongate sheath 102 may be configured to tear along the longitudinal scoring 122 in order to peel-away when the hub 110 is broken and peeled away by pulling the wings 118a and 118b away from each other. The first hub portion 112 may include a second notch (e.g., 126 in FIG. 4) opposite the first notch 114. In such cases, the second notch is also fractured by pulling the wings 118a and 118b away from each other. The elongate sheath 102 may further include a second longitudinal scoring (not shown) at which the hub 110 may be broken and torn.

The first hub portion 112 and the second hub portion 116 may be comprised of material having different material properties. The first hub portion 112 may have different surface properties, durometer, ultimate or tensile strength, modulus of elasticity or other material properties than the second hub portion 116. The second hub portion 116 may be more rigid, stiffer, tougher, or harder, relative to the first hub portion 112. The different material properties of the first hub portion 112 relative to the second hub portion 116 allow the hub 110 to be increased in size to accommodate larger pumps and medical devices while still able to be efficiently broken by the medical personnel's hands. In some implementations, the material forming the second hub portion 16 has an ultimate strength that is greater than an ultimate strength of the material forming the first hub portion 12. In some implementations, the material forming the second hub portion 16 has a rigidity that is greater than a rigidity of the material forming the first hub portion 12. In certain implementations, the first material forming the first hub portion 12 has a hardness of 45 Shore D. In some implementations, the first material may have a hardness of 30 Shore D, 35 Shore D, 40 Shore D, 45 Shore D, 50 Shore D, or any other suitable hardness. In some implementations, the second material forming the second hub portion 16 has a hardness of 60 Shore D, 65 Shore D, 68 Shore D, 70 Shore D, 72 Shore D, 75 Shore D, or any other suitable hardness.

Figure 3:
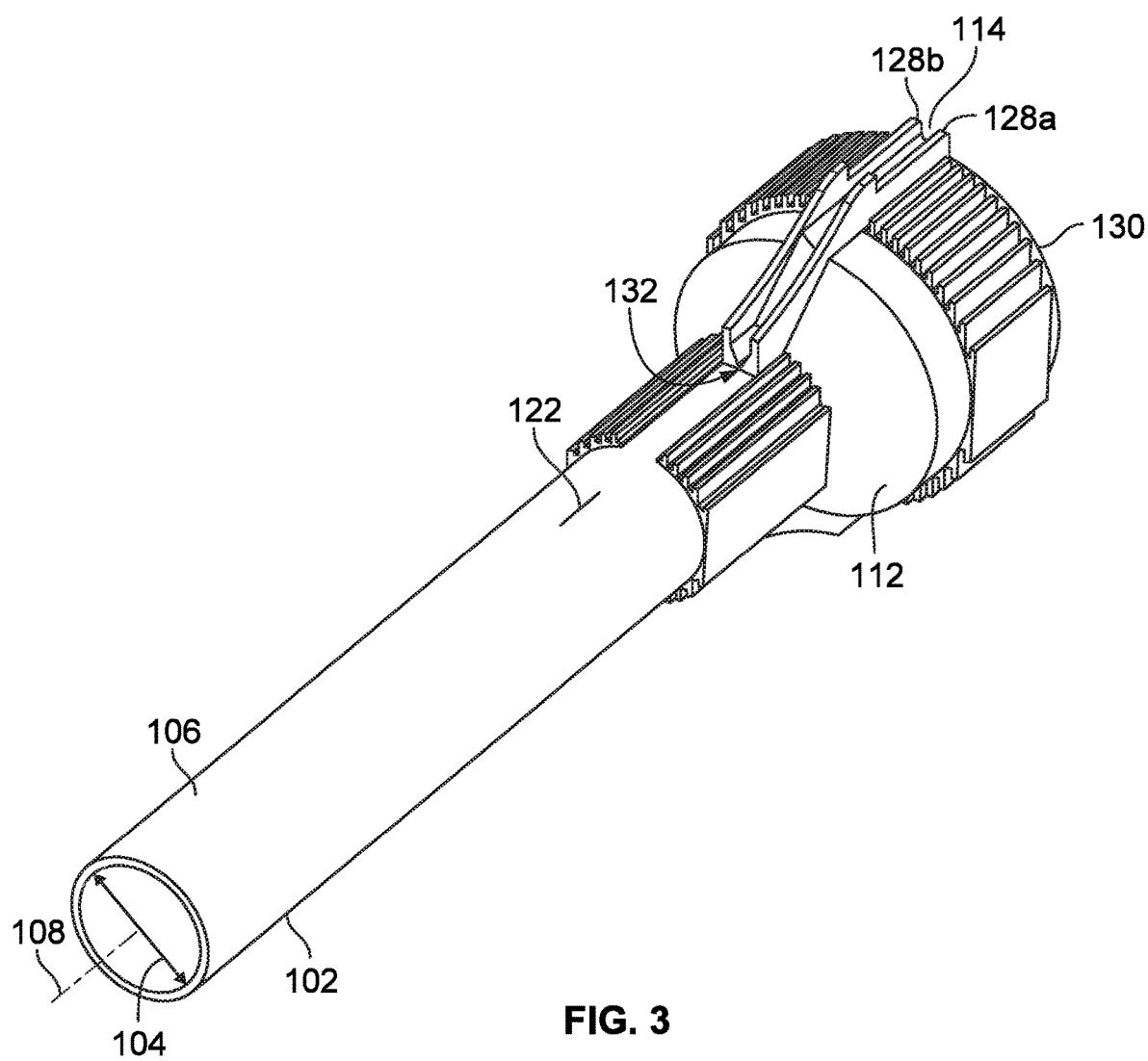
FIG. 3 shows a perspective view of an illustrative first hub portion of an introducer hub assembly.

FIG. 3 shows a perspective view of the first hub portion 112 of the introducer hub assembly 100 of FIG. 2. The first hub portion 112 is attached to the elongate sheath 102 at a proximal end of the elongate sheath 102 and includes a first notch 114 defined by a first ridge 128a and a second ridge 128b, and ridges 130. The first notch 114 may be aligned with a longitudinal scoring 122 on the elongate sheath 102 parallel to the longitudinal axis 108 of the elongate sheath 102. The first hub portion 112 may define the first notch 114 with a minimum thickness 132 of the first hub portion 112 at the first notch 114. The first notch 114 may be further described by the first ridge 128a and the second ridge 128b. The ridges 130 may be constructed as ribbed features or grooves oriented in a direction or many directions on the first hub portion 112. The ridges 130 allow the first hub portion 112 to more securely interface with an over-molded layer, promoting rigidity of the structure during breaking of the introducer hub assembly 100. The ridges 130 provide a mechanical interlock between the first hub portion 112 and the second hub portion (e.g., 116 in FIG. 2) to transmit torque applied to the wings (e.g., 118a and 118b in FIG. 2) to the first hub portion 112. The force applied to the wings (e.g., 118a and 118b in FIG. 2) is thus transmitted to a break wall of the first notch 114. The first hub portion 112 may form a hemostatic bond with the elongate sheath 102, in particular if the first hub portion 112 and the elongate sheath 102 are both comprised of a same material.

Figure 4:
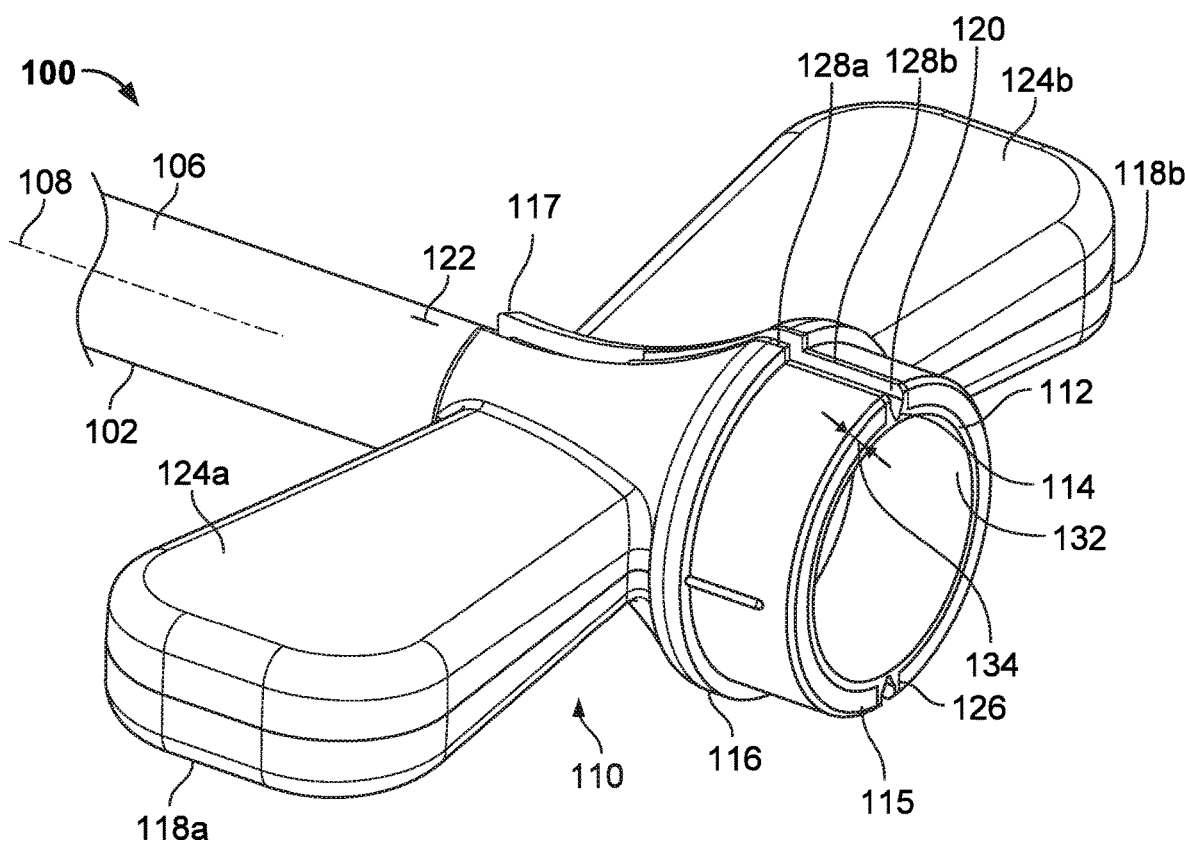
FIG. 4 shows a perspective view of an introducer hub assembly including first and second hub portions.

FIG. 4 shows a perspective view of the introducer hub assembly 100 according to certain embodiments. The introducer hub assembly 100 includes an elongate sheath 102, the first hub portion 112 having a first notch 114 and a second notch 126, and the second hub portion 116 having two wings 118a and 118b. The first hub portion 112 has a proximal end portion 115 and a distal end portion 117. The first hub portion 112 is connected to the elongate sheath 102 at the distal end portion 117. The second hub portion 116 partially covers the first hub portion 112. In some implementations, the second hub portion 112 covers the first hub portion 116 in near entirety except at an opening 120 above the first notch 114. In some implementations, the second hub portion may cover a smaller portion of the first hub portion 112. As described above, the first and second hub portions can be formed using various techniques (e.g., over-molding the second hub portion 116 onto the first hub portion 112 or molding the first and second hub portions 112, 116 separately and then fixing them together using adhesives).

The first notch 114 is oriented parallel to a longitudinal axis 108 of the elongate sheath 102 and is in line with a longitudinal scoring 122 of the elongate sheath 102 such that the hub assembly 100 may function as a peel-away introducer upon breaking of the hub 110 at the first notch 114 and tearing of the elongate sheath 102 along the longitudinal scoring 122. The hub 110 has a second notch 126 in the first hub portion 112 shown on an opposite side of the hub 110 as the first notch 114. The second notch 126 further facilitates breaking of the hub 110 for removal of the hub assembly 100. The second notch 126 may be defined in a similar way as the first notch 114 and may also be oriented to be parallel to the longitudinal axis 108 of the elongate sheath 102. The longitudinal sheath 102 may include a second longitudinal scoring (not shown) which is aligned with the second notch 126 and is opposite the longitudinal scoring 122.

During removal of the introducer assembly 100 a force is applied to the wings 118a and 118b pushing the wide faces 124a and 124b of the wings 118a and 118b toward each other. As the force is transferred through the material and applied toward the first notch 114, there is a compressive force in the hub at the first notch 114 and a tension at the second notch 126 such that both the first notch 114 is broken. Application of a force to the wings in the opposite direction breaks the second notch 126. The first notch 114 in the first hub portion 112 and the minimum thickness 132 of the first hub portion 112 at the first notch 114 and second notch 126 allows the hub 110 to be easily broken at the first notch 114 and second notch 126. The first hub portion may comprise a material having a low ultimate strength to further facilitate the breaking of the hub 110 at the first notch 114 and the second notch 126. The second hub portion 116 may comprise a material having a higher ultimate strength than the material of the first hub portion 112. In some implementations, the first hub portion 112 and the second hub portion 116 may be comprised of polyether block amide (e.g., PEBAX® manufactured by Arkema Group) or similar material. The second hub portion 116 includes the wings 118a and 118b which are able to withstand the force required to break the hub 110 without flexing, facilitating breaking of the hub. Further, the second hub portion 116 may have an increased thickness 134 where it covers the first hub portion 112 in order to provide rigidity to the hub 110.

Figure 5:
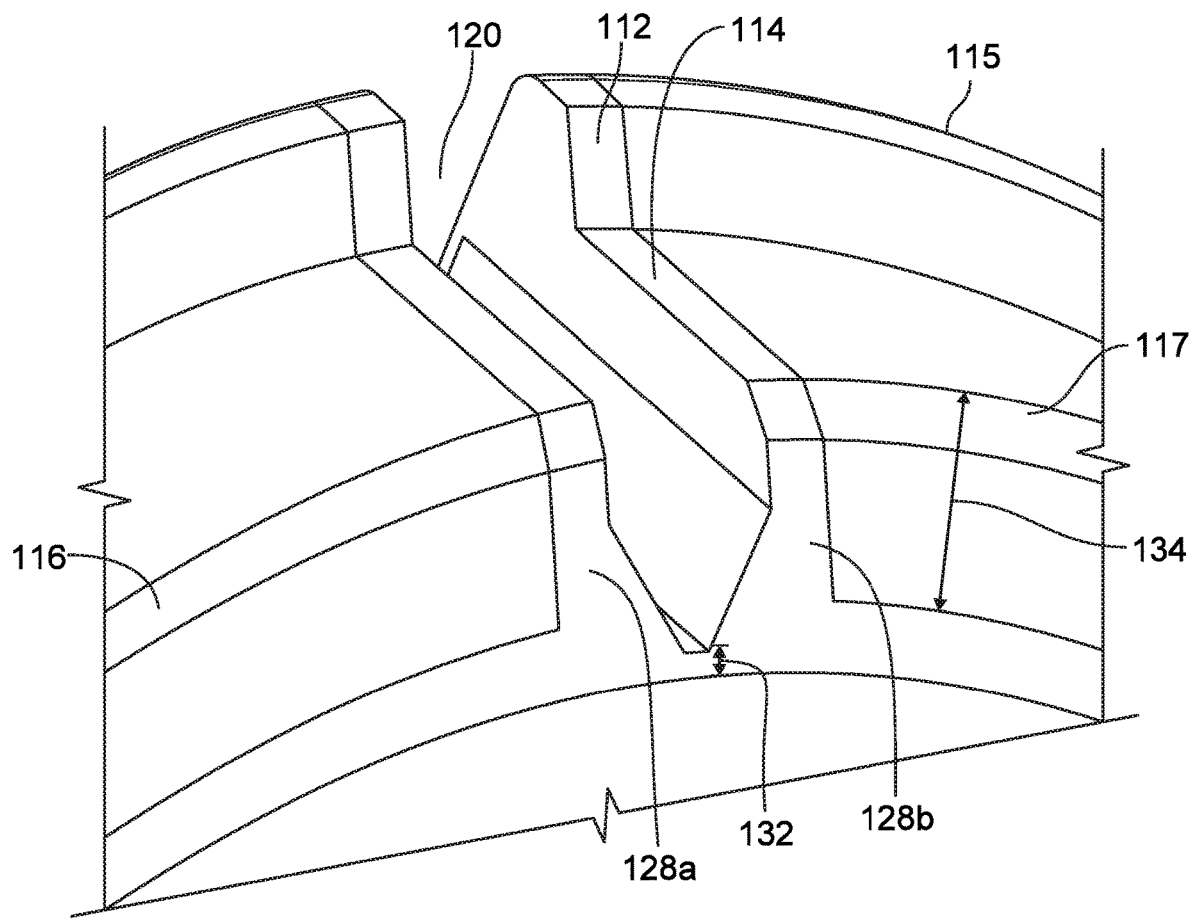
FIG. 5 shows a perspective view of a notch of the introducer hub assembly of FIG. 2.

FIG. 5 shows a perspective view of the first notch 114 in the introducer hub assembly 100 of FIGS. 1 and 2. The first notch 114 is formed in the first hub portion 112 having a minimum thickness 132 at the first notch 114. The first notch 114 runs the length of the first hub portion 112 from the proximal end portion 115 to the distal end portion 117. The first notch 114 is further defined by a first and second ridge 128a and 128b formed in the first hub portion 112. The second hub portion 116 partially covers the first hub portion 112 and includes an opening 120 over the first notch 114. The second hub portion 116 may have an associated thickness 134. In some implementations the first hub portion 112 has a minimum thickness 132 of 0.1 mm at the first notch 114. In some implementations, the first hub portion 112 has a maximum thickness of 0.3 mm at the first notch 114. In certain implementations, the first hub portion 112 has a thickness 132 at the first notch 114 of 0.075 mm, 0.08 mm, 0.09 mm, 0.1 mm, 0.15 mm, 0.2 mm, 0.25 mm, 0.3 mm, 0.35 mm, or any other suitable thickness.

In some implementations, the first hub portion 112 has a variable thickness 132 at the first notch 114 along the length of the first notch 114. In certain implementations, the first hub portion 112 has a greater thickness 132 at the proximal end portion 115 of the first hub portion 112 than at the distal end portion 117. The distal end portion 117 of the notch 114 nearest the connection between the hub 110 and the elongate sheath 102 can have the maximum stress concentration during fracture and may therefore be the intended initiation point of the break. Thus, a relatively thin break wall of the notch 114 at the distal end portion 117 reduces the force required to start the break.

In some implementations, a hemostatic valve (not shown) is included in the hub 110 at the proximal end portion 115. The proximal end portion 115 in which the valve is disposed must be strong enough to support the hoop stress induced in the hub 110 from compression of the valve. This is especially important when objects, such as catheters, are inserted through the hub, increasing the hoop stress. In some implementations, the thickness 132 of the notch 114 at the proximal end portion 115 is greater than the thickness of the notch 114 at the distal end portion 117. The increased notch thickness at the proximal end portion 115 reinforces the hub 110 in the area of increased hoop stress. In some implementations, the thickness of the notch 114 at the distal end portion 117 is around 0.004"-0.006". In some implementations, the thickness of the notch 114 at distal end portion 117 is 0.003", 0.0035", 0.004", 0.0045", 0.005", 0.0055", 0.006", 0.0065" or any other suitable thickness. In some implementations, the thickness of the notch 114 at the proximal end portion 115 of the first hub portion 112 is around 0.010"-0.012". In some implementations, the thickness of the notch 114 at the proximal end portion 115 of the first hub portion 112 is 0.0095", 0.010", 0.0105", 0.011", 0.0115", 0.012", 0.0125" or any other suitable thickness. In some implementations, the change in thickness may occur over a smooth transition. In some implementations, the change in thickness may occur via a series of steps of increased thickness.

The use of the softer material to form the first hub portion 112 allows the variation in the thickness of the notch 114 along its length. This is because the thickness of the notch 114 is constrained on the upper end by the maximum allowable break force and on the lower end by manufacturing tolerances. If the notch 114 is too thick, it cannot be broken. But if it is too thin, it cannot be easily manufactured by traditional processes (e.g., injection molding). The use of a softer material for the first hub portion 112 increases the upper limit for the notch thickness because it enables sufficiently low break force at greater notch thicknesses. This increase in the upper limit of the notch thickness affords a range within which the notch thickness can vary, thereby enabling variation in the notch thickness along the length of the notch. Thus, the use of a different material for the first hub portion 112 compared to the second hub portion 116 enables varying the thickness of the notch along the length of the notch.

Figure 6:
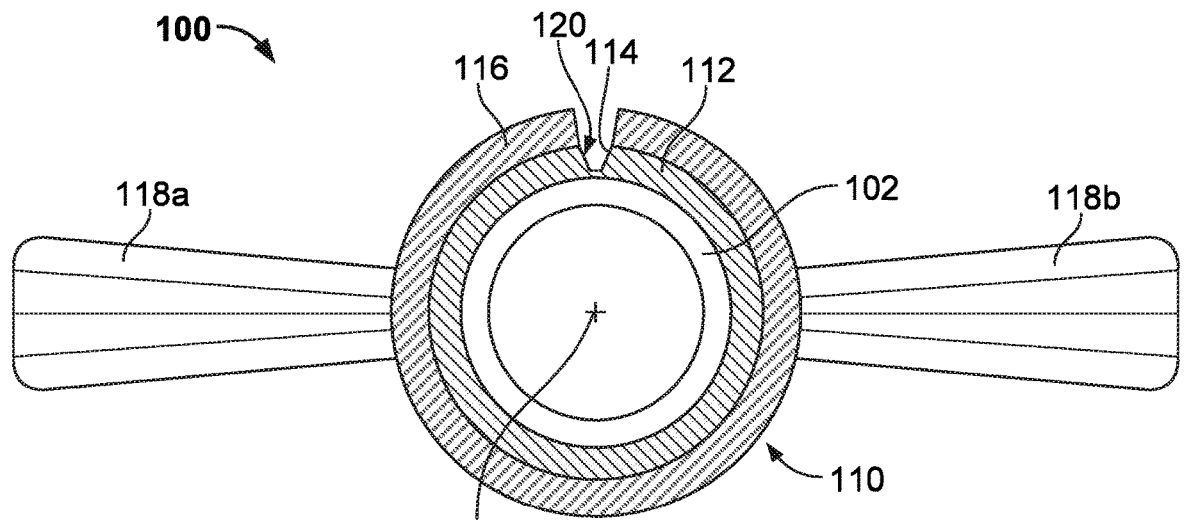
FIG. 6 shows an end view of an illustrative introducer hub assembly having multiple layers of material.

FIG. 6 shows a perspective view along the longitudinal axis 108 of the elongate sheath 102 of an introducer hub assembly 100 according to certain embodiments. The introducer hub assembly 100 includes the elongate sheath 102 sized to fit a heart pump or medical device and to be inserted into a blood vessel of a patient. The elongate sheath 102 is surrounded by the first hub portion 112 including a first notch 114 at which point the thickness of the first hub portion 112 may be at a minimum thickness 132. A second hub portion 116 surrounds the first hub portion 112 and includes an opening 120 over the first notch 114. In some implementations, the first notch 114 may be further defined by a ridge or extension of the first hub portion 112 (shown as 128a and 128b in FIG. 5). In some implementations, a base of the first notch 114 may be defined by the first hub portion 112 and the second hub portion 116 may further define an upper portion of the first notch 114. The second hub portion 116 also includes a first wing 118a and a second wing 118b.

Figure 7:
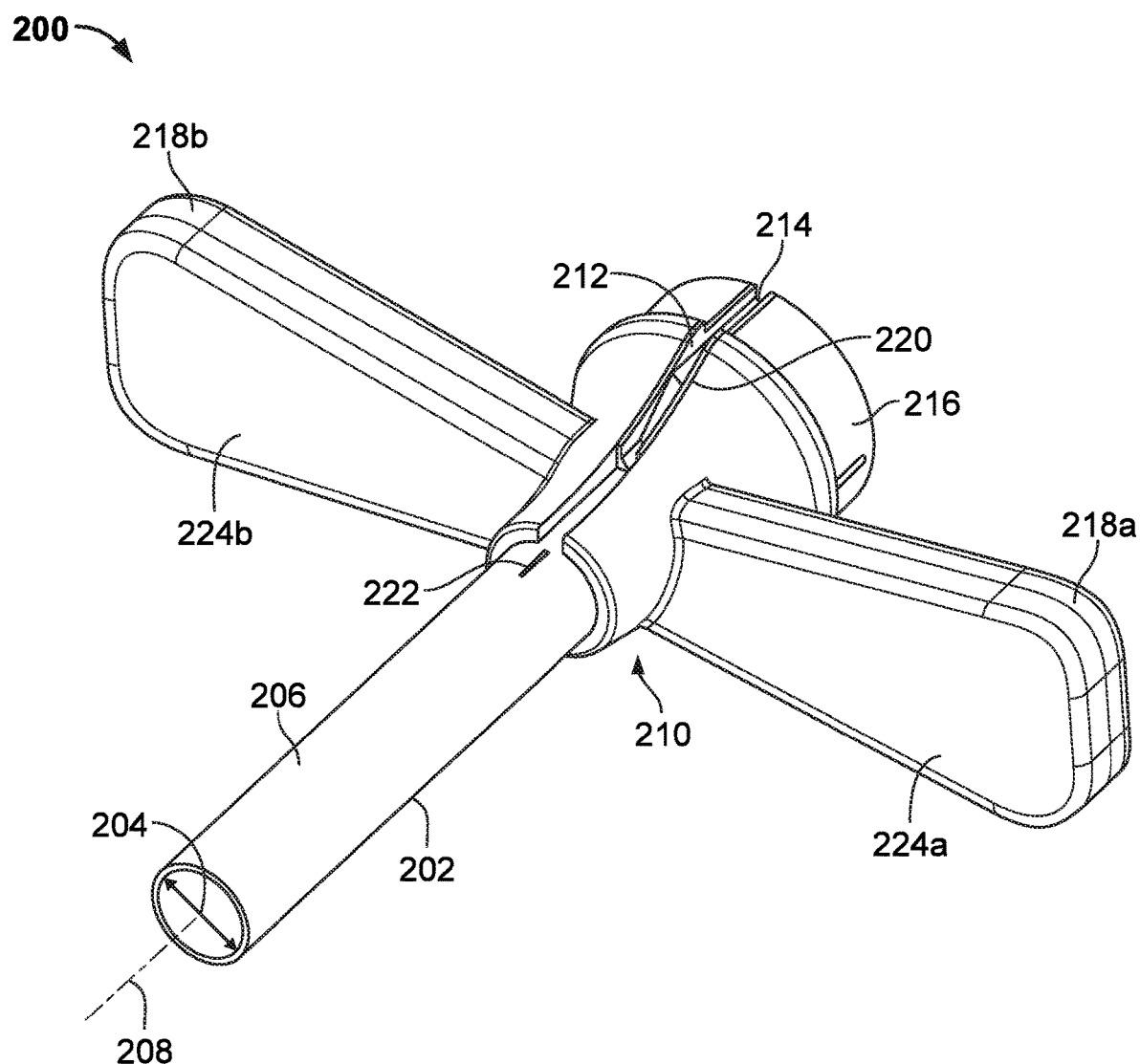
FIG. 7 shows a perspective view of an illustrative introducer hub assembly with wings positioned in a transverse orientation relative to a central longitudinal axis of the introducer hub.

FIG. 7 shows a perspective view of an alternative embodiment of the introducer hub assembly 200 with wings 218a and 218b having a transverse orientation. The introducer hub assembly 200 includes an elongate sheath 202 having an inner diameter 204 sized to allow the passage of a heart pump into a blood vessel of a patient and a longitudinal axis 208, a first hub portion 212 having a first notch 214, and a second hub portion 216 having an opening 220 over the first notch 214 and first and second wings 218a and 218b.

The first wing 218a and the second wing 218b are oriented such that wide faces 224a and 224b of the wings 218a and 218b are normal to the longitudinal axis 208 of the elongate sheath 202. In this embodiment, the introducer hub assembly 200 is fractured and separated from the patient using a different technique than for the embodiment of FIG. 1. More specifically, to break the hub 210 at the first notch 214, the wide faces 224a and 224b of the wings 218a and 218b are forced toward the elongate sheath 202. The hub 210 fractures along the first notch 214 and along a second notch (not shown) opposite the first notch 214. Additionally, the elongate sheath 202 tears at a longitudinal scoring 222 and at a second longitudinal scoring (not shown) which is opposite the longitudinal scoring 222. The introducer hub assembly 200 is now broken in half and can be removed, leaving the device, catheter or guidewire in place in a blood vessel of a patient.

Figure 8:
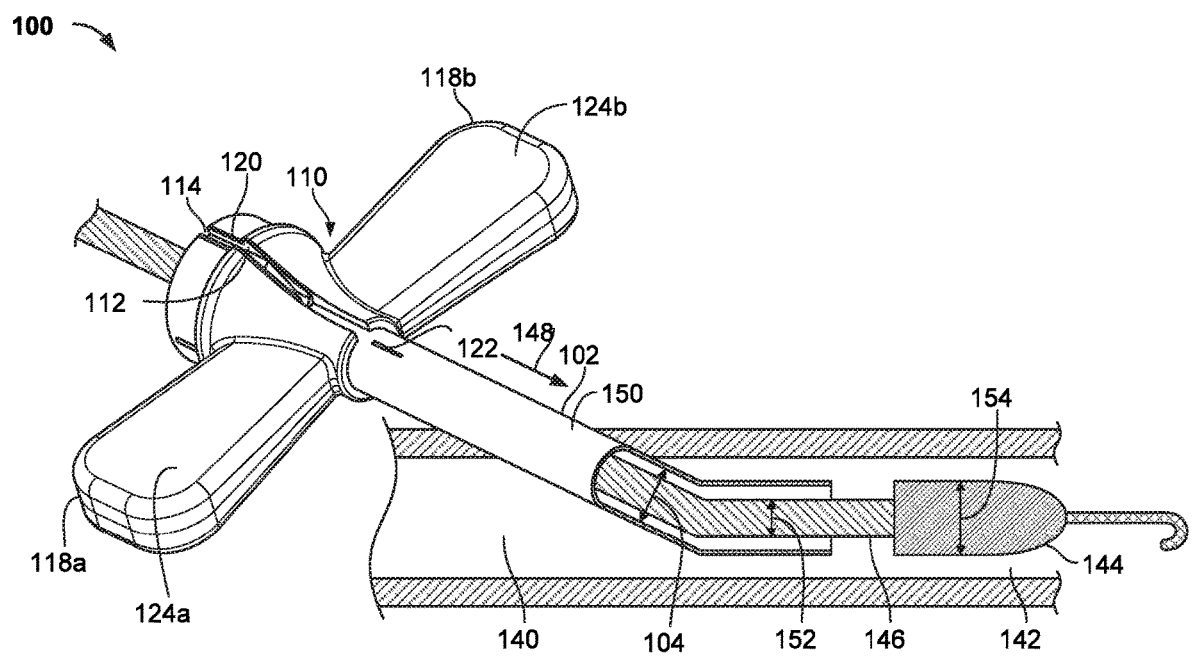
FIG. 8 shows an introducer hub assembly inserted into a blood vessel of a patient with a percutaneous pump extending therethrough.

FIG. 8 shows the introducer hub assembly 100 of FIGS. 2, 4 and 6 inserted into a blood vessel of a patient 140 with a percutaneous pump 142 extending partially therethrough. The percutaneous pump 142 can include various features, such as a pump head 144 and a catheter body 146. The percutaneous pump 142 may be an intravascular heart pump, a heart pump driven by a flexible shaft and a motor positioned external to the patient's body, a heart pump including an implantable motor, a heart pump having an expandable pump rotor, or any other suitable pump. The introducer hub assembly 100 is advanced into the blood vessel 140 through the blood vessel aperture 150 in the direction indicated by arrow 148 and then the percutaneous pump 142 is inserted through the introducer hub assembly 100 and into the blood vessel 140. The blood vessel 140 may be a femoral artery, and the blood vessel aperture 150 may be an arteriotomy.

After the percutaneous pump 142 has been advanced through the introducer hub assembly 100 the introducer hub assembly 100 may be removed and in some implementations replaced by a device appropriate for longer-term use. To remove the introducer hub assembly, a healthcare professional may grasp the first and second wings 118a and 118b and apply a force to the wings 118a and 118b in a direction either toward the elongate sheath 102 or a direction radial to the elongate sheath 102 forcing a first wing 118a toward the second wing 118b depending on the orientations of the first and second wings 118a and 118b relative to the elongate sheath 102. In the orientation of wings 118a and 118b shown, the healthcare professional applies a radial force (radial with respect to the elongate sheath 102) to the wings 118a and 118b to move them toward each other. The first and second wings 118a and 118b are formed of a stiff material of the second hub portion 116 and do not flex when force is applied. The applied force is transmitted from the wings 118a and 118b to the first notch 114 and the second notch 126 (not shown). The minimum thickness 132 of the first hub portion 112 at the first notch 114 and second notch 126 allows the hub 110 to be broken at the first notch 114 and second notch 126. In some implementations, the healthcare professional applies a second radial force in an opposite direction in order to break the second notch 126. The longitudinal scoring 122 on the elongate sheath 102 allows the sheath to separate along the longitudinal axis 208, and the hub 110 and elongate sheath 102 may be peeled away in two pieces leaving the percutaneous pump 142 in place in the blood vessel 140.

The foregoing is merely illustrative of the principles of the disclosure, and the apparatuses can be practiced by other than the described embodiments, which are presented for purposes of illustration and not of limitation. It is to be understood that the apparatuses disclosed herein, while shown for use in percutaneous insertion of heart pumps, may be applied to apparatuses in other applications requiring hemostasis.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

I claim:

1. An introducer assembly comprising:
   an elongate sheath sized for insertion into a blood vessel of a patient, the elongate sheath having a longitudinal axis;
   a hub coupled to a proximal portion of the elongate sheath, the hub comprising:
   a first hub portion having a first notch wherein the first hub portion includes a first ridge and a second ridge that define edges of the first notch, wherein the first ridge and the second ridge extend laterally from the first hub portion;
   a second hub portion partially surrounding the first hub portion, the second hub portion comprising:
   two wings; and
   an opening disposed above the first notch; and
   wherein the first hub portion comprises a first material and the second hub portion comprises a second material, the first material differing from the second material.

2. The introducer assembly of claim 1, wherein the first material has a first ultimate strength and the second material has a second ultimate strength, the second ultimate strength being greater than the first ultimate strength.

3. The introducer assembly of claim 1, wherein the first material has a first stiffness and the second material has a second stiffness, the second stiffness being greater than the first stiffness.

4. The introducer assembly of claim 1, wherein the first notch is oriented parallel to the longitudinal axis of the elongate sheath.

5. The introducer assembly of claim 1, wherein the hub is configured to break at the first notch along a direction of the longitudinal axis of the elongate sheath.

6. The introducer assembly of claim 1, wherein the elongate sheath further comprises a longitudinal scoring parallel to the longitudinal axis of the elongate sheath.

7. The introducer assembly of claim 6, wherein the elongate sheath is configured to tear along the longitudinal scoring parallel to the longitudinal axis of the elongate sheath.

8. The introducer assembly of claim 1, wherein the first hub portion and the elongate sheath form a hemostatic bond wherein the hemostatic bond is configured to prevent blood from flowing between the first hub portion and the elongate sheath.

9. The introducer assembly of claim 1, wherein the wings each comprise a wide face and a narrow face, and the wide face is normal to the longitudinal axis of the elongate sheath.

10. The introducer assembly of claim 1, wherein the wings each comprise a wide face and a narrow face, and the narrow face is normal to the longitudinal axis of the elongate sheath.

11. The introducer assembly of claim 10, wherein the first hub portion comprises a second notch.

12. The introducer assembly of claim 1, wherein the first material has a hardness of about 45 Shore D.

13. The introducer assembly of claim 1, wherein the second material has a hardness in a range of about 68-72 Shore D.

14. The introducer assembly of claim 1, wherein the hub has a minimum diameter of about 9 Fr.

15. The introducer assembly of claim 1, wherein the first hub portion has a minimum thickness of 0.1 mm at the first notch.

16. The introducer assembly of claim 1, wherein the first hub portion has a thickness at the first notch that is variable along a length of the first notch.

17. The introducer assembly of claim 16, wherein the thickness of the first hub portion at the first notch is greatest at a proximal end portion of the first hub portion.

18. The introducer assembly of claim 17, wherein the thickness of the first hub portion at the first notch is between about 0.01 inches and 0.012 inches at the proximal end portion of the first hub portion.

19. The introducer assembly of claim 17, wherein the thickness of the first hub portion at the first notch is between about 0.004 inches and 0.006 inches at a distal end portion of the first hub portion.

* * * * *